United States Patent [19]
Marquez et al.

[11] Patent Number: 5,374,596
[45] Date of Patent: * Dec. 20, 1994

[54] PROCESS FOR TREATING ALUMINA

[75] Inventors: Marco A. Marquez, Caracas; Jose C. Gonzalez; Victor J. Degouveia, both of San Antonio de Los Altos; Francisco Yanez, La Candelana Caracas, all of Venezuela

[73] Assignee: Intevep, S.A., Caracas, Venezuela

[*] Notice: The portion of the term of this patent subsequent to May 11, 2010 has been disclaimed.

[21] Appl. No.: 8,630

[22] Filed: Jan. 25, 1993

Related U.S. Application Data

[62] Division of Ser. No. 847,194, Mar. 6, 1992, Pat. No. 5,210,326.

[51] Int. Cl.$^5$ .......................... B01J 38/56; B01J 20/34
[52] U.S. Cl. ........................................ 502/29; 502/31
[58] Field of Search .................. 502/415, 31, 29; 423/628; 568/697, 698, 699; 44/449, 448, 447

[56] References Cited

U.S. PATENT DOCUMENTS

| | | | |
|---|---|---|---|
| 2,754,344 | 7/1956 | Weatherly | 502/31 |
| 4,390,413 | 6/1983 | O'Rear et al. | 568/697 |
| 4,755,499 | 7/1988 | Neal et al. | 502/415 |
| 4,795,545 | 1/1989 | Schmidt | 208/91 |
| 4,846,962 | 7/1989 | Yao | 208/31 |
| 5,120,881 | 6/1992 | Rosenfeld et al. | 568/697 |
| 5,210,326 | 5/1993 | Marquez et al. | 568/697 |

Primary Examiner—Paul E. Konopka
Attorney, Agent, or Firm—Bachman & LaPointe

[57] ABSTRACT

A process for treating alumina mediums used for purifying a hydrocarbon feedstock employed in a process for the production of ether-rich additives for gasoline.

1 Claim, 3 Drawing Sheets

PROCESS FOR TREATING ALUMINA

This is a division of application Ser. No. 847,194 filed Mar. 6,1992, now U.S. Pat. No. 5,210,326.

BACKGROUND OF THE INVENTION

The present invention relates to a process for the production of ether-rich additives for gasoline, and, more particularly, the production of MTBE, TAME or mixtures thereof from light hydrocarbon streams.

MTBE, TAME or mixtures thereof are used extensively as fuel extenders and octane value improving agents in the production of unleaded gasoline. Generally, but for the inclusion of such fuel extenders and octane value improving agents, acceptable octane values can only be obtained by varying the compounding additives in the gasoline, that is, increasing the lead content of the gasoline. The desirability of lead free gasolines is clearly recognized. Lead additives in gasolines result in the emission of pollutants in exhaust gases from internal combustion engines thereby contributing to overall environmental pollution. The employment of substitutes for lead in gasoline compounds which improve the octane value of the gasoline will lead to a cleaner burning gasoline thereby improving air quality and the overall environmental condition.

There are many processes developed in the prior art for producing MTBE (methyl t-butyl ether) and TAME (methyl t-amyl ether). Typical etherification processes are disclosed in U.S. Pat. Nos. 5,001,292; 4,925,455; 4,827,045; and 4,830,635 to Harandi et al. Other known processes include that disclosed in U.S. Pat. 4,025,989 to Hagan et al. For the most part, these known processes for preparing ethers as additives for gasoline comprise reacting a primary alcohol, such as methanol, with an olefin having a double bond on a tertiary carbon atom, such as, isobutylene and isopropentene. It is known in the prior art to react the alcohol and the olefin in the presence of a catalyst. Suitable known catalysts include Lewis acids (sulfuric acid) and organic acids (alkyl and aryl sulfonic acids). A particularly suitable catalyst for these reactions are ion exchange resins in their acid form of the type marketed under the trademark "AMBERLIST 15" which is a trademark of Rohm and Haas or Bayer product K2631. While many hydrocarbon feedstocks may be used for the manufacture of MTBE and TAME it is particularly useful in the petroleum refining operation to process MTBE and TAME from light hydrocarbon streams resulting from fluid catalytic cracking (FCC) refinery operations. When processing FCC hydrocarbon streams under etherification conditions so as to form MTBE and TAME it has been found that the catalysts used in the process are rapidly poisoned, that is, the catalysts are deactivated. As the catalyst materials used in known processes are relatively expensive, the foregoing problem of catalyst deactivation leads to not only process inefficiency but also substantial increases in processing costs. None of the prior art processes, and particularly none of the U.S. Patents discussed above, deal with the aforesaid problem or suggest solutions thereto.

Naturally, it would be highly desirable to provide a process for the conversion of hydrocarbon streams, particularly light naphtha hydrocarbon streams from FCC refinery processes, to MTBE and TAME which overcome the problems of catalyst poisoning as discussed above.

Accordingly, it is the principal object of the present invention to provide a process for the conversion of liquid light hydrocarbon streams to ether-rich additives such as MTBE and TAME in an efficient and economic manner.

It is a particular object of the present invention to provide a process as aforesaid wherein the poisoning of the catalysts used in the etherification process is inhibited.

It is a further object of the present invention to provide a process as aforesaid wherein the liquid light hydrocarbon feedstock fed to the etherification zone is pretreated with an alumina medium prior to etherification processing in the presence of the catalyst.

It is a still further object of the present invention to provide a process as aforesaid wherein the alumina medium used in the process of the present invention is readily regenerated for further use in the process.

Further objects and advantages of the present invention will appear hereinbelow.

SUMMARY OF THE INVENTION

In accordance with the present invention the foregoing objects and advantages are readily obtained.

The present invention relates to a process for the production of ether-rich additives from light hydrocarbon feedstocks and, more particularly, from light hydrocarbon feedstocks having significant concentrations of nitrogen compounds, mercaptan and water. Such feedstocks include light naphtha cut hydrocarbons from FCC processes. The liquid hydrocarbon feedstocks are passed through a medium for removing the nitrogen compounds, particularly nitriles, mercaptan and water from the feedstock so as to form a purified feedstock prior to subjecting the feedstock to etherification process conditions in the presence of the catalyst. In accordance with the present invention, the liquid hydrocarbon feedstock is passed through a superactivated alumina medium where nitrogen compounds, particularly nitriles, mercaptan and water are removed so as to result in a purified feedstock to the etherification zone which is substantially free of nitrogen compounds, mercaptan and water. It has been found in accordance with the present invention that by pretreating the light hydrocarbon feedstock as aforesaid, the rate of poisoning of the catalyst employed in the etherification process is greatly reduced thereby increasing process efficiency while at the same time decreasing processing costs.

The process of the present invention, in its preferred form, provides for a plurality of superactivated alumina mediums wherein the feedstock being treated is passed through one of the plurality of superactivated alumina mediums for purifying same. The purified filtered feedstock is monitored downstream of the alumina medium for sensing when the first alumina medium is spent. When the first alumina medium is spent the feedstock is passed through another of the plurality of alumina mediums so as to allow the process to proceed in a continuous manner. The spent alumina medium is then subjected to a regeneration process in accordance with the present invention.

The spent superactivated alumina medium is regenerated by draining the liquid hydrocarbon feedstock from the alumina medium which is in the form of a bed of porous alumina particles forming interstitial spaces therebetween. The drained bed of alumina particles is thereafter dried with inert gas. In accordance with the present invention, the drained and dried alumina medium is thereafter washed under critical conditions with an organic solvent in a series of steps to remove polymer precursors and prohibit the formation of polymers. The washed alumina media free of polymers is thereafter dried with inert gas in a series of steps.

The process of the present invention wherein the feedstock to the etherification reactor is pretreated so as to remove nitrogen compounds, particularly nitriles, mercaptan and water allows for the efficient and economical production of ether-rich additives such as MTBE and TAME by improving the life of the catalyst used in the etherification process. In addition, by providing a process for regenerating the medium used in the pretreatment of the feedstock the overall process of the present invention is efficient and economical to carry out.

DETAILED DESCRIPTION OF THE INVENTION

Figure 1:
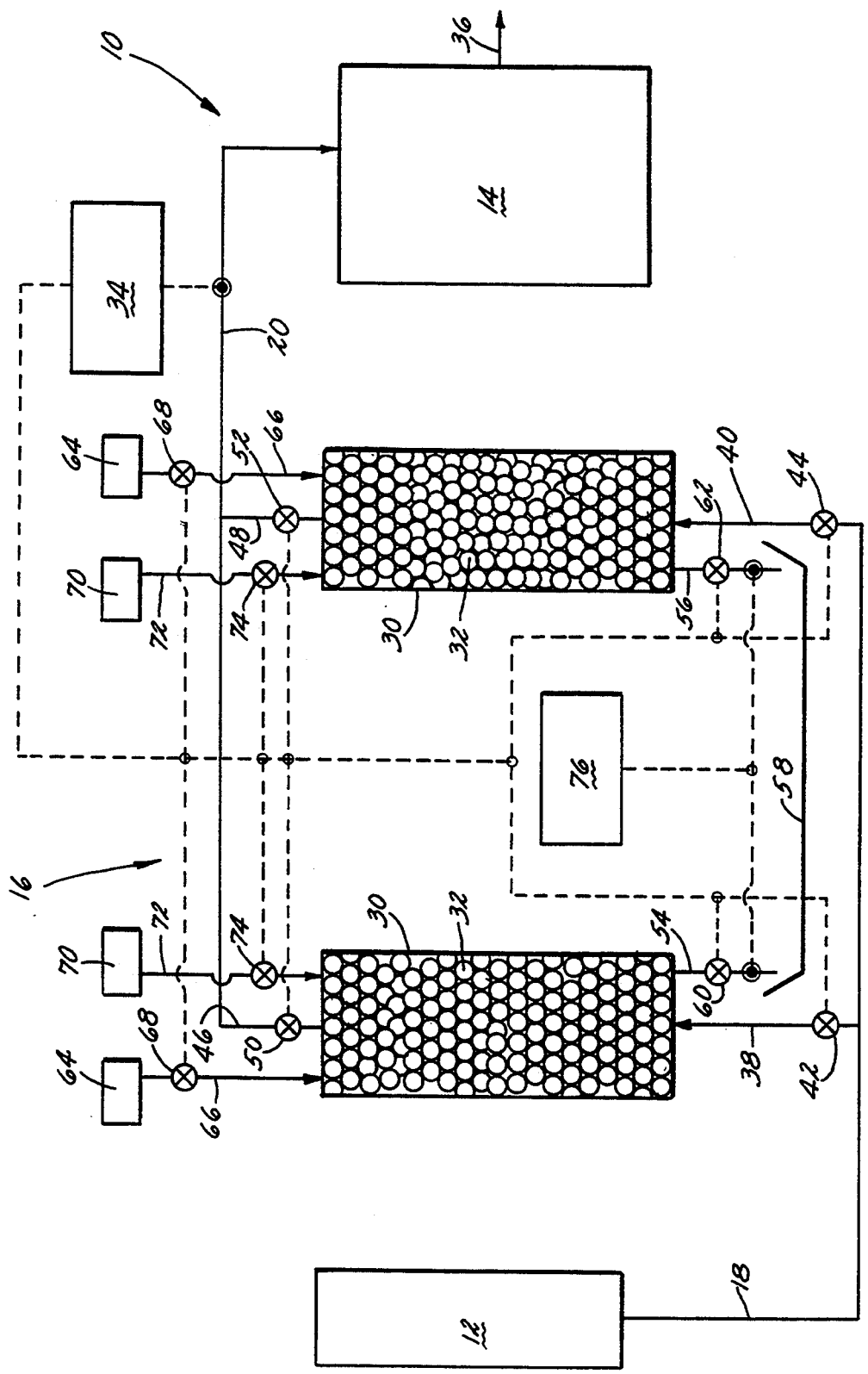
FIG. 1 is a schematic flow diagram illustrating the process of the present invention.

With reference to FIG. 1, the process of the present invention will be described in detail.

A facility 10 for carrying out the conversion of light hydrocarbon feedstocks to an ether-rich additive, particularly TAME and MTBE, is illustrated. For purposes of description the process of the present invention will be described with reference to light hydrocarbon feedstocks obtained from FCC process operations, particularly, light naphtha cut FCC feeds which are cut in the $C_3$-$C_7$ range and preferably $C_4$ and $C_5$ range.

With reference to FIG. 1, the feedstock from the FCC refinery facility 12 is fed to the etherification zone 14 for converting the light hydrocarbon feedstock to an ether-rich additive, particularly, MTBE and TAME. In accordance with the process of the present invention, the feedstock from the FCC process 12 is pretreated prior to feeding same to the etherification zone 14 in purification zone 16 for removing nitrogen compounds, particularly nitriles, mercaptan and water from the light hydrocarbon feedstock produced by the FCC process in zone 12.

In accordance with the present invention, the typical feedstock produced in the FCC refinery facility 12 which is drawn off via line 18 is a light hydrocarbon naphtha feedstock. In accordance with the preferred embodiment of the present invention the light naphtha cut is $C_3$-$C_7$ cut and preferably substantially a $C_4$, $C_5$ cut. The feedstock described above for the etherification zone 14 which is produced in the FCC refinery facility 12 and drawn off via line 18 is characterized by the following composition: isobutene in the range of 10-15 wt. %; isoamylenes in the range of 7-14 wt. %; diolefins in the range of 0.5-1.0 wt. %; a mercaptan concentration in the range of 4-6 ppm; a nitrogen concentration in the range of 17-20 ppm wherein nitriles are present in the range of 15-17 ppm; and water content in the range of about 30-50 ppm.

In accordance with the present invention the feed from the FCC refinery facility 12 is fed to a purification zone 16 prior to delivery to the etherification zone 14 for removing nitriles and other nitrogen compounds, mercaptan and water from the feedstock so as to produce a purified feedstock substantially free of nitrogen compounds, particularly nitriles, mercaptan and water for delivery from the purification zone 16 via line 20 to the etherification zone 14. In accordance with the preferred embodiment of the present invention, the purified feedstock from the purification zone 16 which is fed via line 20 to the etherification zone 14 has a total nitrogen content of less than 2 ppm wherein the nitrile content is less than 1 ppm, a total mercaptan content of less than 1 ppm and a water content of less than 1 ppm. It has been found, in accordance with the process of the present invention, that by reducing the nitrogen compounds, mercaptan and water (particularly nitriles) the life of the catalyst used in the etherification process in zone 14 is greatly improved. It has been found that the nitriles in the feedstock decompose in the etherification zone in the presence of water to form amines which deactivate the catalyst employed in the etherification process, that is, poison the catalyst.

The feedstock from the FCC facility 12 is treated in the purification zone 16 by passing the feedstock via line 18 through an alumina medium held in an absorption zone or trap 30. In accordance with the present invention a plurality of traps or zones 30 are employed in the process of the present invention in a manner to be described hereinbelow. The alumina medium employed in the process of the present invention comprises a bed of porous alumina particles 32 which form interstitial spaces therebetween when packed into the absorption zone 30. A particularly suitable alumina medium for use in the process is sold under the trademark SELEXSORB CD and is commercially available from ALCOA. Typically, the feedstock is passed through the alumina medium at a liquid space velocity (LHSV) in the range of about 1.0 to about 5.5 v/v/hr. The process conditions are typically pressure in the range of 100-300 psi and temperature in the range of 50-200° F.

The purified feedstock leaving the trap or zone 30 is continually monitored by means of a sensor 34 (to be described in detail hereinbelow) in order to insure that the feedstock delivered via line 20 to the etherification zone 14 for processing therein has a total nitrogen content less than 2 ppm wherein the nitriles content is less than 1 ppm, a mercaptan content of less than 1 ppm, and a water content of less than 1 ppm. The purified feedstock from absorption zone 30 is delivered to the etherification zone 14 via line 20 wherein the feedstock is processed under typical etherification conditions in the presence of a catalyst so as to produce ether-rich additives, particularly, MTBE and TAME. The catalyst employed in the etherification zone 14 is in the form an acidic ion exchange resin and a suitable ion exchange resin catalyst is commercially available under the name AMBERLIST from Rohm and Haas or Bayer product K2631. The process conditions in the etherification zone 14 are typically as follows: pressure in the range of 150-300 psi, a temperature in the range of 120-150° F, a methanol to isoalkene ratio in the range of about 1.05-1.50 mole/mole, and a ratio of $H_2$ to diolefins in the range of 1.5 to 3.2 moles/moles. The ether-rich additive produced in the etherification zone 14 is discharged via line 36. Depending on the nature of the feedstock to the etherification zone 14, either MTBE or TAME or a mixture of the two is produced and discharged via line 36. For example, if the feed to the etherification zone 14 is substantially rich in $C_4$, the product produced is MTBE. If the feedstock is an FCC cut rich in $C_5$, the resulting ether-rich additive is TAME. If the FCC cut feedstock is a mixture of $C_3$-$C_7$ hydrocarbons, the product of the etherification zone 36 is a mixture of MTBE and TAME compounds.

In accordance with the present invention, it is preferred that the purification zone 16 be provided with a plurality of absorption zones or traps 30 for purifying the feedstock delivered via line 18 from the FCC refining facility 12. By providing a plurality of absorption zones 30 the process can be carried out in a continuous manner wherein the feedstock delivered via line 18 may be treated in one of the absorption zones 30 while the deactivated purifying alumina medium in the other absorption zone 30 is regenerated in accordance with the present invention to a superactivated alumina medium as described hereinbelow.

For purposes of illustration the purification zone 16 is illustrated in FIG. 1 as having two absorption zones 30. Each of the absorption zones 30 are selectively fed with feedstock from line 18 via lines 38 and 40, respectively. Lines 38 and 40 are provided with valves 42 and 44 respectively for selectively feeding the feedstock from line 18 to one or the other of the absorption zones 30 in a manner to be described hereinbelow. The discharge from the absorption zones 30, that is, the purified feedstock, is drawn off via lines 46 and 48 and delivered to feedline 20 for delivery to the etherification zone 14. Valves 50 and 52 are located in lines 46 and 48 respectively and are selectively operable in the manner described hereinbelow.

Sensor 34 is connected to line 20 and monitors the purity of the discharge from the absorption zones 30 in order to assure that the content of nitrogen, nitriles, mercaptan and water in the purified feedstock delivered to the etherification zone 14 meet the purification levels described above. The sensor 34, which is commercially available and the details of which form no part of the present invention, compares the measured values of the nitrogen compounds, nitriles, mercaptan and water in the feedstock in line 20 to a fixed value concentration having the values described above with regard to the feedstock to the etherification zone. By monitoring the discharge from the absorption traps 30 in the manner aforesaid, it can be determined when one of the alumina medium in one of the absorption traps 30 is spent. Upon sensing that the alumina medium 32 in one of the zones 30 is spent, the sensor, through suitable control means available commercially, may activate valves 42, 44, 50 and 52 so as to divert the flow of feed from line 18 to the other of the zones 30 wherein the process can continue in a uninterrupted manner. The spent alumina medium in the zone or trap 30 not in use in the etherification process can then be regenerated in accordance with the present invention in the manner described hereinbelow.

In accordance with the present invention, the spent alumina media is regenerated by first draining any hydrocarbon feed in the absorption zone 30 from the absorption zone via conduits 54 and 56 to sump 58. Lines 54 and 56 are provided with valves 60 and 62 which are selectively operated by the sensor means 34 in a known manner. Once the hydrocarbon medium is drained from the alumina particle within the absorption zone 30, the alumina particles are flushed and dried with an inert gas delivered from a source 64 via line 66 which is provided with valve 8. The inert gas is preferably at a temperature of less than 110° F. After the alumina particles are dried the alumina medium is subjected to a two-step washing process for regenerating the alumina medium to a superactivated alumina medium for further use in the process. In accordance with the present invention, the dried alumina medium is washed with an organic solvent, preferably toluene, under controlled temperature conditions so as to flush polymer precursors from the medium. It is critical that the temperature in this stage of regeneration be maintained at a temperature less than that temperature which would lead to polymerization of the polymer precursors captive within the alumina medium. Generally, a temperature of less than 122° F. is sufficient; however, a lower temperature may be required depending on the nature of the feedstock treated in the absorption zones 30. With reference to FIG. 1, and for purposes of illustration, the toluene solvent may be delivered from a source 70 via a line 72 provided with a valve 74 to the alumina medium for washing same. The used solvent discharged via conduit 54 is monitored by sensor 76 so as to determine when this first step washing operation is completed. For example, it has been found that when flushing the alumina medium with the toluene solvent, the discharged solvent is initially brownish in color as the polymer precursors are removed and the solvent lightens in color as the amount of polymer precursors removed decreases. Therefore, by monitoring the color of the discharged solvent the first step flushing operation can be completed when the discharged solvent runs substantially clear. This color change can be monitored by sensor 76 which can be any suitable commercially available device. Once the polymer precursors have been substantially removed the alumina medium is thereafter washed again with the organic solvent at an elevated temperature of between 140-250° F. so as to dissolve any polymers formed in the alumina medium during feedstock purification and the first stage washing. This second stage washing is continued until the discharged solvent again runs substantially clean in the manner described above with regard to the first stage washing and sensor element 76. In accordance with the present invention, the solvent is passed through the alumina medium at a ratio with respect to the volume of alumina in the zone 30 of greater than 4 volumes of solvent per volume of alumina and preferably greater than 10 volumes of solvent per volume of alumina. The washed, superactivated alumina medium is thereafter dried with the inert gas supplied via line 66 from source 64 at a temperature of typically between 220 and 500° F. and preferably in two steps from a lower temperature to a higher temperature. After drying the superactivated alumina medium it is cooled and is now ready for use in the etherification process of the present invention.

The sensor 34 operates the valves 42, 44, 50, 52, 60, 62, 68, and 74 through suitable control means known in the art (shown by dash lines) for selectively controlling the flow of the feedstock via line 18, inert gas via lines 66 and solvent via lines 72 during the various operation stages of the process of the present invention.

For clarity, the process of the present invention will now be described in a step by step manner. With valves 42 and 50 in their open position and valves and 44 and 52 in their closed position, feedstock from FCC refining facility 12 is delivered via line 18 into one of the absorption traps 30 of purification zone 16 for contacting the feed with the alumina medium 32 in the trap 30. The purified discharge from the trap 30 is delivered via line 20 to the etherification zone 14 for processing of same for the production of ether-rich additives. In accordance with the present invention, the feedstock fed to the etherification zone 14 via line 20 has the maximum nitrogen content, nitrile content, mercaptan content and water content set forth above. Sensor 34 continually monitors the purified feedstock in line 20 in order to insure the necessary purity. When the measured values of nitrogen, nitriles, mercaptan and water approaches a fixed value the sensor, sensing the foregoing with associated control means closes valves 42 and 50 and opens valves 44 and 52 so as to divert flow of the feedstock in line 18 to another of the absorption traps 30 within purification zone 16. Thus, the feed to the etherification zone 14 is continuous and non-interrupted. The spent alumina medium in the first absorption trap 30 is thereafter regenerated by the sequential steps of drying with inert gas and two-step washing with organic solvent in the manner described in detail above. When the alumina medium in the second absorption trap becomes spent as determined by sensor 34, valves 44 and 52 are closed and valves 42 and 50 are opened so as to direct the feedstock from line 18 through the now regenerated alumina medium in the first absorption zone 30. The spent alumina in the second zone may now be regenerated in the manner described above. It should be appreciated that the number of absorption zones 30 may be increased as required so as to insure continuous operation of the process and allow for sufficient regeneration of the spent alumina prior to the need of using the spent alumina again in the process scheme.

As can be seen from the foregoing, the process of the present invention allows for the pretreatment of the feedstock to the etherification zone in a continuous uninterrupted manner. The advantages and superior results obtained by the process of the present invention will be made clear hereinbelow from a consideration of the following illustrative examples.

EXAMPLE I

Figure 2:
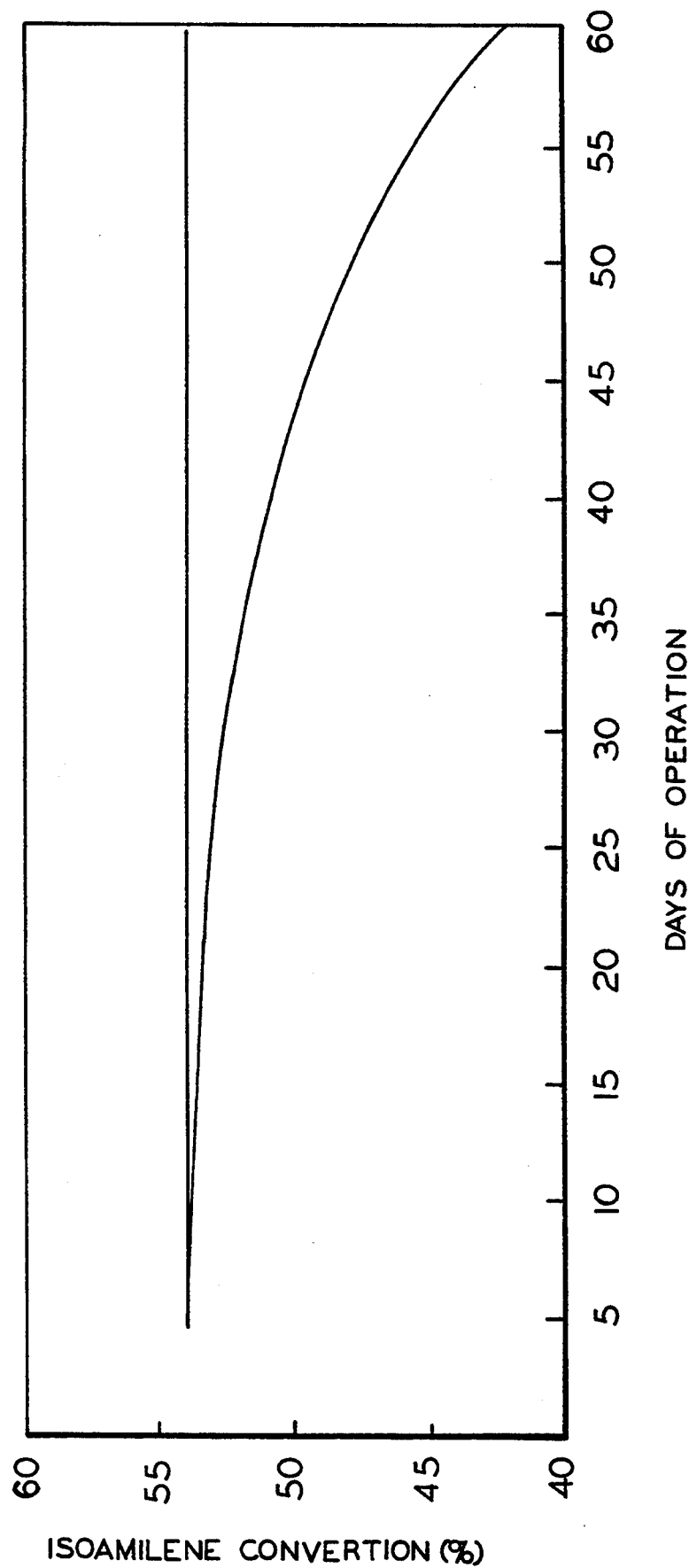
FIG. 2 is a graph demonstrating the adverse effect of nitriles on the acid catalyst activity used in the etherification of light hydrocarbon feedstocks to TAME and demonstrates the advantages of the process of the present invention.

In order to demonstrate the poisoning effect of nitrogen compounds and particularly nitriles such as propionitriles and acetonitriles on the catalyst employed in the etherification process, an untreated FCC feedstock rich in $C_5$ and having the composition set forth in Table I below was subject to etherification in the presence of an AMBERLIST or Bayer product K2631 ion exchange catalyst under the process and conditions set forth below in Table II. FIG. 2 shows the conversion of the feedstock to the ether-enriched product TAME over time. In order to demonstrate the benefits of pretreatment in accordance with the present invention, the same feedstock was pretreated with a porous alumina bed (SELEXSORB CD alumina sold by ALCOA) to obtain a purified feedstock having the concentration of mercaptan, total nitrogen, and nitrile concentration described below in Table I. This purified feedstock was thereafter subjected to etherification under the same process conditions set forth in Table II. The results of the effect of this feedstock on the feedstock conversion to TAME and thus the deterioration of the catalyst used in the etherification process is illustrated in FIG. 2. It can be seen from FIG. 2 that after 60 days the effectiveness on conversion of the catalyst employed in the etherification process when processing a purified feedstock treated in accordance with the present invention is substantially identical to that obtained from the virgin catalyst while the conversion effectiveness of the catalyst when processing a feedstock which was not treated in accordance with the present invention decreases substantially over time. This example clearly illustrates the effectiveness of the pretreatment of the feedstock in accordance with the present invention to remove nitrogen, nitrile, mercaptan and water in accordance with the present invention.

TABLE I

| FEEDING | UNTREATED | TREATED |
| --- | --- | --- |
| Isobutene (% wt) | 8.20 | 8.00 |
| Isoamylenes (% wt) | 10.10 | 10.10 |
| Diolefins (% wt) | 0.83 | 0.77 |
| Mercaptan (ppm) | 5.00 | less than 1 |
| Nitrogen Total (ppm) | 18.00 | less than 2 |
| Nitriles (ppm) | 17.00 | less than 1 |
| Nitrogen Basic (ppm) | less than 1 | less than 1 |

TABLE II

| | |
| --- | --- |
| Temperature of feeding | 132 degrees F. |
| Process Pressure | 175–200 psig |
| LHSV | 2 V/V/hr |
| Ratio MeOH/ISOALKENES | 1.05 ml/ml |

EXAMPLE II

In order to demonstrate the efficiency of the regeneration process of the present invention for regenerating the porous alumina medium used in the process of the present invention, a spent alumina medium employed in the etherification process of the present invention was regenerated in accordance with the present invention and compared to a new virgin alumina product. The alumina medium employed was a commercially available alumina medium sold by ALCOA under the name SELEXSORB CD. The spent alumina media was processed in accordance with the parameters set forth below in Table III. The spent alumina medium was first drained of all liquid hydrocarbon feedstock and thereafter dried with an inert gas, nitrogen, at a temperature of 100° F. for 1 hour. The dried alumina medium was thereafter washed with toluene in the first stage at a temperature of 100° F for 2.5 hours. The volume of toluene employed in the first step washing operation was in a ratio of 5 volumes of toluene per volume of catalyst. The alumina medium was thereafter subjected to a second washing step at a temperature of 175° F. for an additional period of 2.5 hours. The volume of solvent employed in the second washing step was identical to that employed in the first washing step. The alumina medium was thereafter purged and dried for 4 hours with nitrogen at a temperature of 250° F. and thereafter the temperature of the inert gas was raised to 500° F. and the alumina was dried for 12 hours resulting in a superactivated alumina product in accordance with the present invention.

TABLE III

| | TIME (H) | TEMP (F.) | N2 (N/H) | TOLUENE (L/H) |
| --- | --- | --- | --- | --- |
| Drying | 1 | 100 | 180–300 | — |
| Washing 1 | 2.5 | 100 | — | 5 |
| Washing 2 | 2.5 | 175 | — | 5 |
| Purging | 4 | 248 | 180–300 | — |

TABLE III-continued

|  | TIME (H) | TEMP (F.) | N2 (N/H) | TOLUENE (L/H) |
| --- | --- | --- | --- | --- |
| Desorption | 12 | 500 | 180–300 | — |

Figure 3:
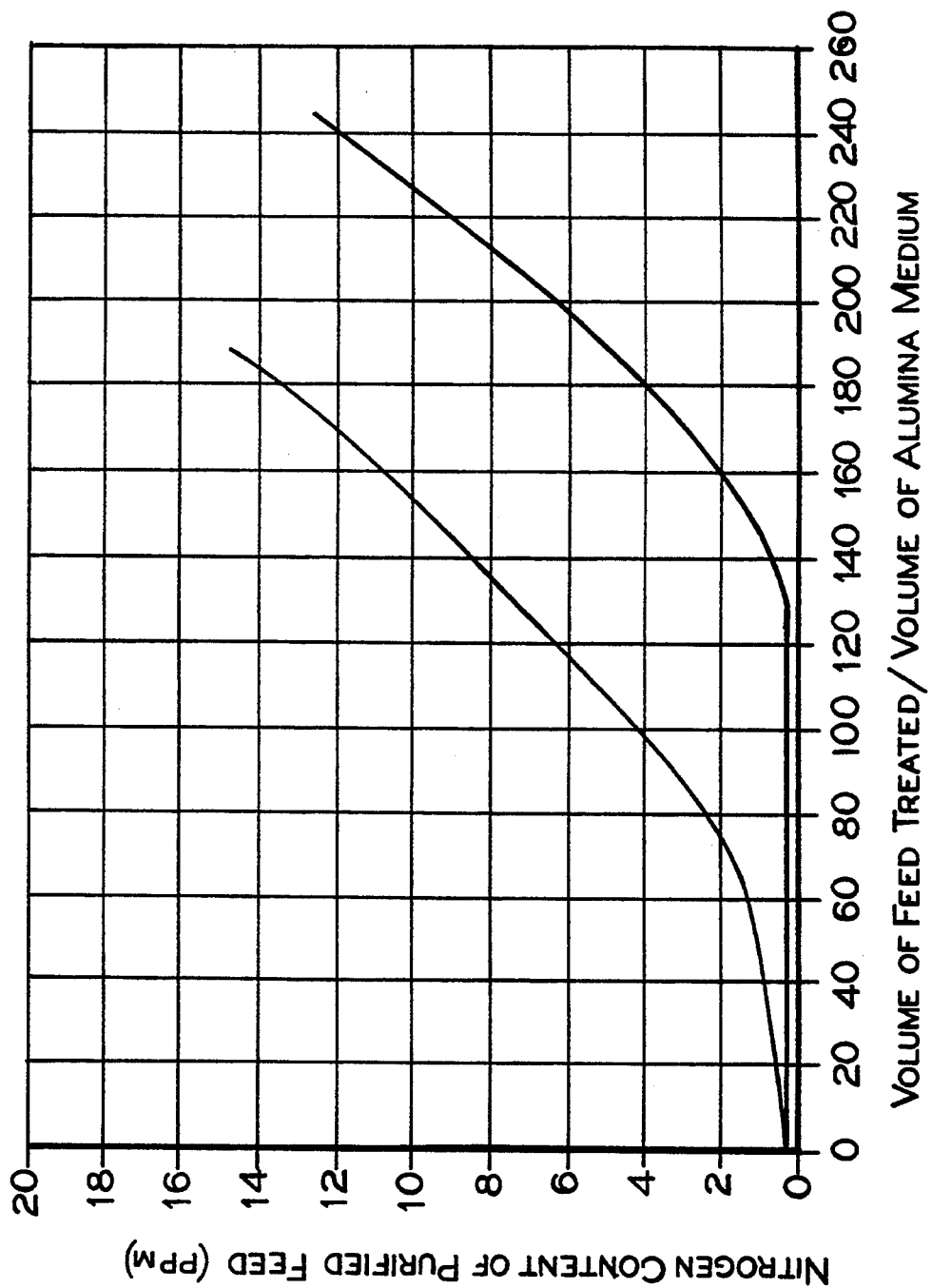
FIG. 3 illustrates the positive effect of the regeneration process of the present invention on the nitrile absorption capabilities of an alumina medium treated in accordance with the process of the present invention.

The regenerated alumina medium was thereafter used to treat the feedstock described above in Example I and compared to a virgin alumina medium used to pretreat the same feedstock under the conditions described above in Example I. FIG. 3 shows the results of this test. It is clear from FIG. 3 that the alumina medium regenerated in accordance with the process of the present invention exhibits superior absorption capabilities for nitrogen and nitriles when compared to conventional virgin alumina.

As can be seen from the foregoing, the process of the present invention provides for an effective and economical process for producing ether-rich additives such as TAME and MTBE from light hydrocarbon feedstocks.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A process for treating commercial porous alumina particles poisoned with nitrogen compounds including polymer precursors absorbed during the pretreatment of light hydrocarbon feedstocks for use in an etherification process so as to form a superactivated alumina comprising the steps of:
   (1) drying said alumina particles by passing an inert gas through said alumina particles at a temperature of not greater than 110° F.;
   (2) washing said porous alumina particles with an organic solvent at a temperature of less than 122° F. so as to flush polymer precursors from said alumina while avoiding the formation of polymers within the porous alumina;
   (3) sensing when the porous alumina is substantially free of said polymer precursors; and
   (4) thereafter further flushing said porous alumina particles with an organic solvent at a temperature of about between 140° to 250° F. so as to dissolve polymers within said porous alumina while maintaining said solvent in a liquid phase.

* * * * *